(12) United States Patent
Ting et al.

(10) Patent No.: US 6,882,896 B2
(45) Date of Patent: Apr. 19, 2005

(54) METHOD FOR CLASSIFYING A SUBSTRATE

(75) Inventors: Chin-Lung Ting, Tainan (TW); Chun-Bin Wen, Tainan (TW)

(73) Assignee: Chi Mei Optoelectronics Corporation, Tainan (TW)

( * ) Notice: Subject to any disclaimer, the term of this patent is extended or adjusted under 35 U.S.C. 154(b) by 446 days.

(21) Appl. No.: 10/064,484

(22) Filed: Jul. 18, 2002

(65) Prior Publication Data

US 2003/0208455 A1 Nov. 6, 2003

(30) Foreign Application Priority Data

May 3, 2002 (TW) ........................... 91109283 A

(51) Int. Cl.$^7$ ........................... G06F 19/00; H01L 21/66

(52) U.S. Cl. ........................... 700/121; 700/110; 438/14; 702/82

(58) Field of Search ................. 700/108–110, 117–121; 382/141, 148, 149; 356/237.1, 239.1, 239.2, 237.2–237.5; 438/14, 16, 17; 702/81–84

(56) References Cited

U.S. PATENT DOCUMENTS

| | | | | |
|---|---|---|---|---|
| 6,011,619 A | * | 1/2000 | Steffan et al. | 356/237.3 |
| 6,096,093 A | * | 8/2000 | Caywood et al. | 716/21 |
| 6,272,393 B1 | * | 8/2001 | Steffan et al. | 700/121 |
| 6,466,895 B1 | * | 10/2002 | Harvey et al. | 702/181 |
| 6,674,889 B1 | * | 1/2004 | Takayama | 382/149 |
| 6,792,366 B1 | * | 9/2004 | Hosoya et al. | 702/83 |
| 6,792,367 B1 | * | 9/2004 | Hosoya et al. | 702/83 |

FOREIGN PATENT DOCUMENTS

JP 2001-067479 A * 3/2001

* cited by examiner

*Primary Examiner*—Maria N. Von Buhr
(74) *Attorney, Agent, or Firm*—Winston Hsu

(57) ABSTRACT

A method for classifying a substrate first provides the substrate and its corresponding inspection map. Then, a database having a plurality of specification data is provided. After that, the inspection map is compared with each of the specification data so as to find the specification data coinciding with the inspection map. Finally, the substrate is defined according to the layout of active areas coinciding with the inspection map, and then the substrate is classified and stored.

21 Claims, 8 Drawing Sheets

METHOD FOR CLASSIFYING A SUBSTRATE

BACKGROUND OF INVENTION

1. Field of the Invention

The present invention relates to a method for defining active areas of a substrate, and more particularly, to a method for defining active areas of a substrate and classifying the substrate.

2. Description of the Prior Art

A liquid crystal display (LCD) has advantages of full-color displaying, portability, high resolution, and low radiation. It is for these reasons that the LCD is gradually replacing the CRT monitor in desktop computers. A glass substrate, so-called mother glass, is one of the raw materials for manufacturing LCDs. Glass substrates can be divided into alkali glass and non-alkali glass. The alkali glass is used for manufacturing a twisted nematic (TN) or a super twisted nematic (STN) LCD, while the non-alkali is utilized for fabricating a thin film transistor (TFT) LCD. Generally, before a glass substrate is used for making an LCD, a cleaning process is first performed to clean the glass substrate. Then, the glass substrate is sifted for determining whether the glass substrate is suitable for manufacturing an LCD or not. Finally, active areas of the glass substrate are defined, with an active area being a region of the glass substrate suitable for fabricating an LCD thereon.

In the prior art, when sifting glass substrates, a surface scan apparatus is utilized to inspect the number of defects within a region, which is about 10~15 mm away from a periphery of a glass substrate. When the number of defects within the region on the glass substrate is larger than an allowable defect count (e.g. 50/piece), the glass substrate is scrapped. Conversely, when the number of defects within the region on the glass substrate is smaller than the allowable defect count (e.g. 50/piece), the glass substrate can be used to manufacture an LCD.

The surface scan apparatus is to utilize an optical analysis technology to inspect defects, such as particles, scratches, breakages, and so on, on the surface of a glass substrate. A light source, beam splitters, reflectors or detectors is used and thus the surface scan apparatus can scan the surface of the glass substrate to inspect the defects on the surface of the glass substrate. As a glass substrate is examined by the surface scan apparatus, the light source projects inspection light beams onto the surface of the glass substrate. When the inspection light beams scan a defect, the inspection light beams are then scattered by the defect. Then, the scattered light beams are received and analyzed by a detector for clarifying and recording a size and a position of the defect. Finally, after the surface scan apparatus finishes scanning the glass substrate, the inspecting results of the glass substrate are recorded in an inspection map, which records distributing positions, counts, and sizes of such defects.

Please refer to FIG. 1 and FIG. 2. FIG. 1 is a schematic diagram showing an inspection map of a glass substrate. FIG. 2 is a schematic diagram of active areas of the glass substrate corresponding to the inspection map shown in FIG. 1. As is known to those skilled in the art, an inspection map of a substrate records positions of defects in numeral type or in graphic type. For convenience of explanation, the inspection map described in the following description records positions of defects in graphic type. That is, the inspection map is marked with a symbol, such as a dot, for illustrating each of the defects on the glass substrate. As a result, the number of the symbols in the inspection map represents the defect counts, while positions of the symbols correspond to the positions of the defects.

As shown in FIG. 1 and FIG. 2, the inspection map 10 corresponds to a surface region of the glass substrate 20, a region 12 corresponds to a region 22, which is inspected by the surface scan apparatus, and a dot 14 represents a defect of the surface region of the substrate. There are forty-six dots 14 in the inspection map 10, which represents that there are forty-six defects on the glass substrate 20. Since the defect count is smaller than 50/piece (i.e. the allowable defect count as described above), the glass substrate 20 can be used for manufacturing an LCD and an active area 24 of the glass substrate 20 can be defined according to the size of the LCD.

In the prior method for sifting a glass substrate suitable for manufacturing an LCD, once the number of defects on the glass substrate is larger than an allowable defect count, the glass substrate is scrapped. Therefore, the prior method for sifting a glass substrate always wastes many glass substrates. For example, as shown in FIG. 3, the number of defects on the glass substrate 20 is 53/piece, which is larger than the above-mentioned allowable defect count of 50/piece. Nevertheless, the number of defects within the whole active areas 24 is 6/piece only, and almost all defects are located outside the active areas 24. Actually, the glass substrate 20 shown in FIG. 3 still can be used for manufacturing an LCD, but in the prior method for sifting a glass substrate, the glass substrate shown in FIG. 3 would be scrapped, which results in wasting glass substrates. Especially, as a size of a glass substrate becomes larger and larger, it is more important to effectively utilize the glass substrate. As a result, it is necessary to look for a suitable method for sifting a glass substrate.

SUMMARY OF INVENTION

It is therefore an objective of the invention to provide a method of defining active areas of a substrate and classifying the substrate for solving the above-mentioned problems.

According to the invention, a method for classifying a substrate is provided. A substrate and its inspection map are provided. A database having a plurality of data, each of the data having a layout of active areas and its corresponding allowable defect count, is provided. The inspection map is divided according to each of the layouts of active areas, wherein the divided inspection map is compared with the corresponding allowable defect count of each of the layouts of active areas for classifying the substrate.

It is an advantage that the invention compares the number of defects within active areas of a glass substrate with the allowable defect count of the glass substrate. Since locations of active areas of a glass substrate are defined according to a size of an LCD, thus, active areas corresponding to each type of LCDs are positioned at different regions of the glass substrate. Accordingly, even though the glass substrate is not suitable for manufacturing an 18" LCD, it still may be suitable for fabricating a 15" LCD. As a result, each glass substrate can be utilized more effectively, and yield of the glass substrate is further enhanced.

These and other objectives of the present invention will no doubt become obvious to those of ordinary skill in the art after reading the following detailed description of the preferred embodiment, which is illustrated in the multiple figures and drawings.

Table 1 illustrates an embodiment of the data stored in the database of the present invention.

DETAILED DESCRIPTION

Figure 1:
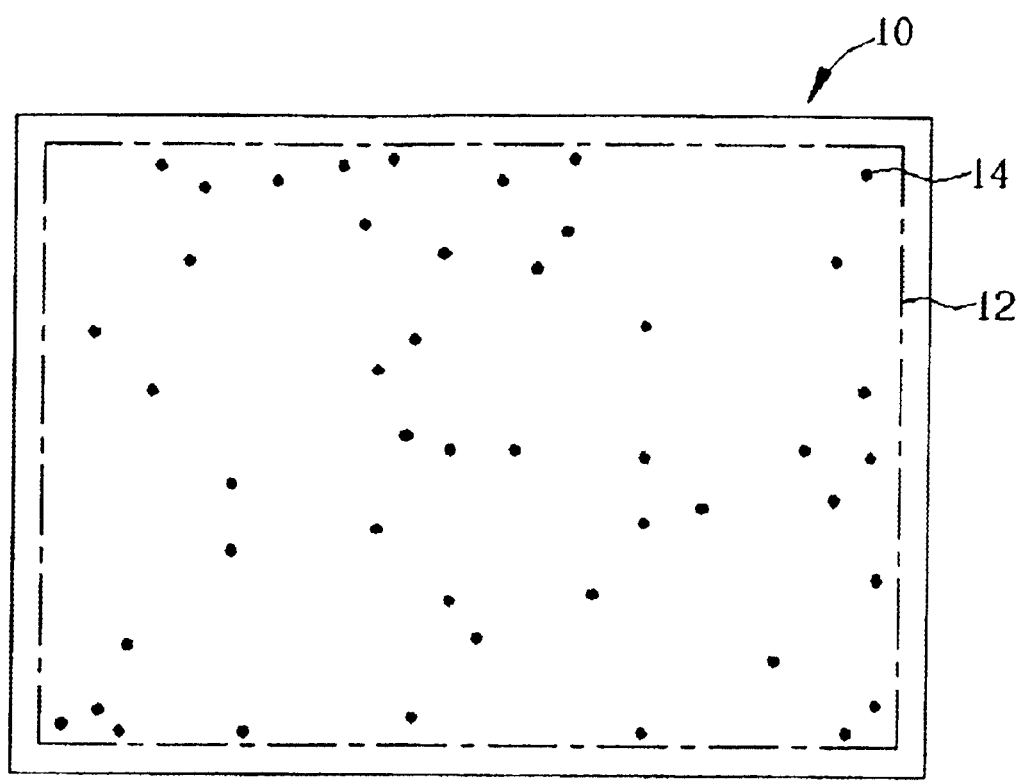
FIG. 1 is a schematic diagram of an inspection map of a glass substrate.
Figure 2:
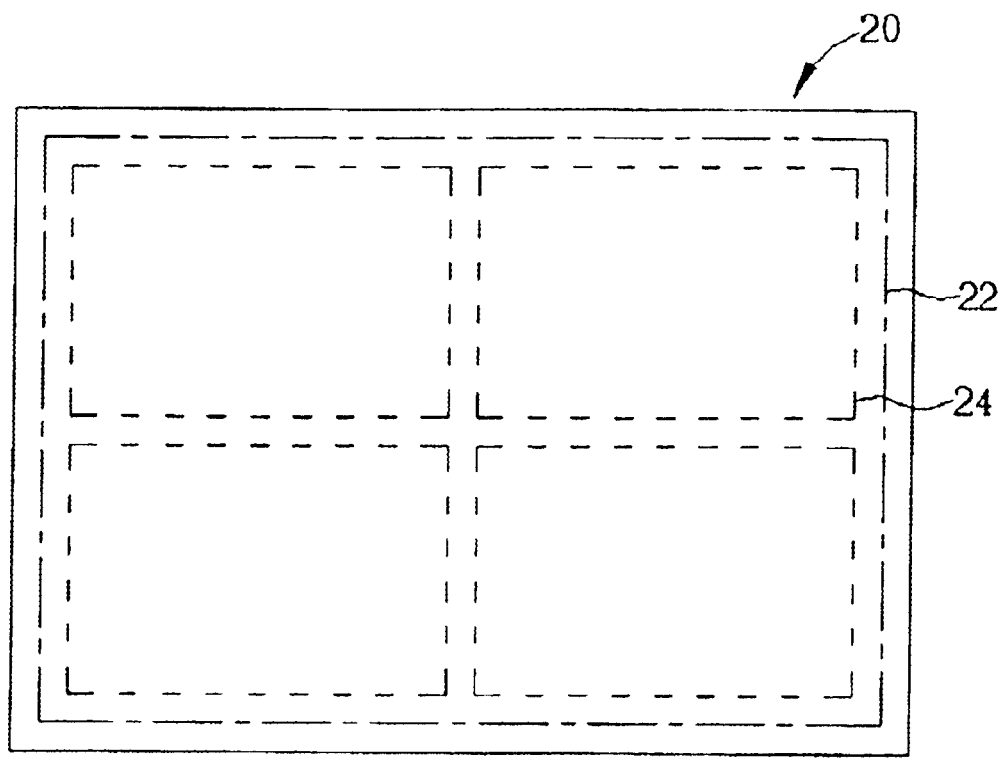
FIG. 2 is a schematic diagram of active areas of the glass substrate corresponding to the inspection map shown in FIG. 1.
Figure 3:
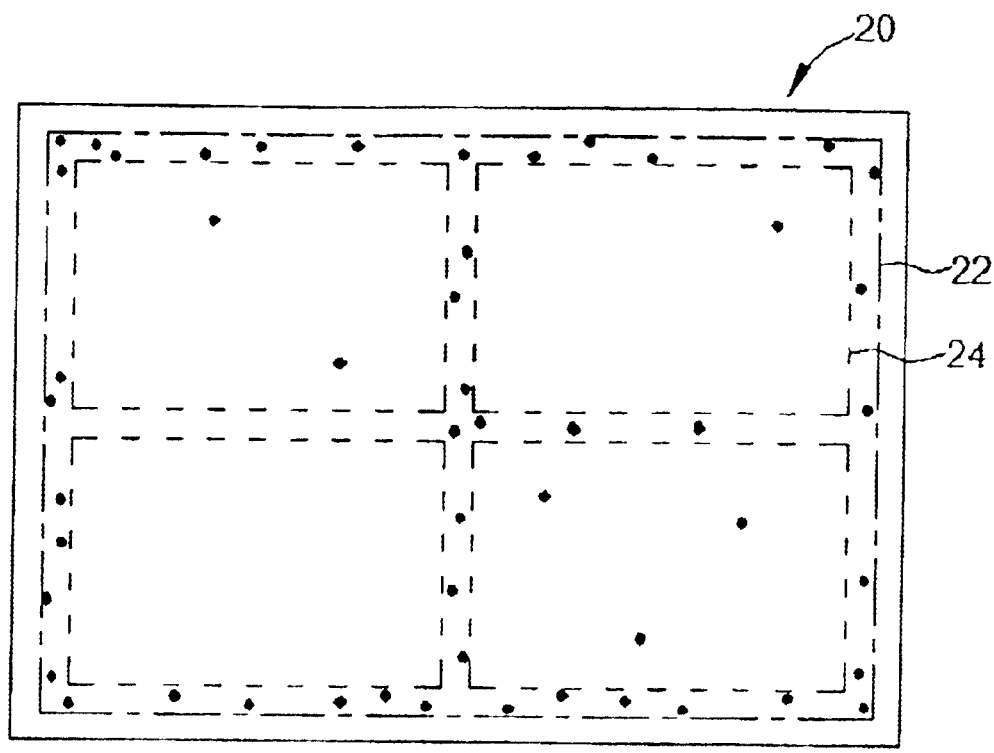
FIG. 3 is a schematic diagram of an inspection map of a glass substrate.
Figure 4:
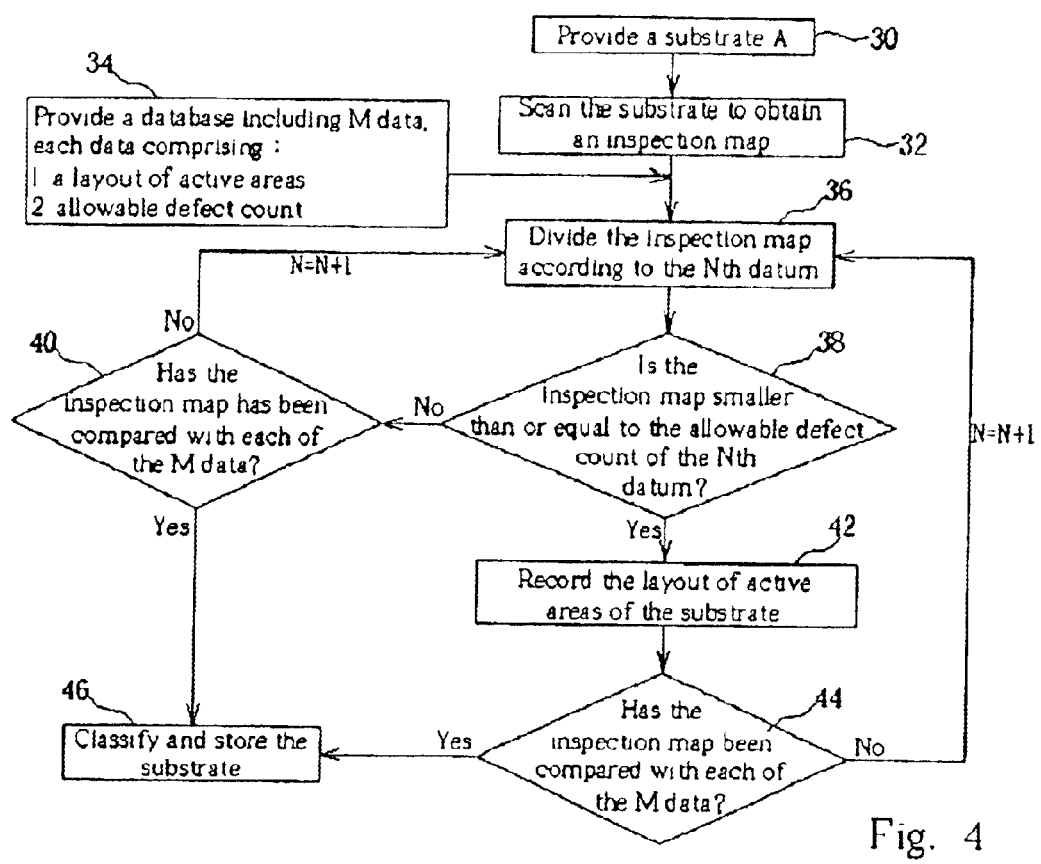
FIG. 4 is a flow chart illustrating a method of defining active areas of a substrate and classifying the substrate.

FIG. 4 is a flow chart illustrating a method of defining active areas of a substrate and classifying the substrate. As shown in FIG. 4, step 30 is firstly performed to provide a substrate A. In the embodiment of the present invention, the substrate A is a glass substrate of an LCD having a dimension of 680 mm×880 mm, for example. In addition, thin film transistors or color filters of the LCD can be formed on the glass substrate in the following processes. Moreover, before a color filter is formed on the glass substrate, a thin film can be formed on the surface of the glass substrate. The thin film can be chromium (Cr) or indium tin oxide (ITO), for example. In another embodiment of the present invention, the substrate A can be a glass substrate of any other flat display panels, such as a plasma display panel (PDP). Additionally, the substrate A can also be a quartz substrate or a semiconductor wafer.

Figure 5:
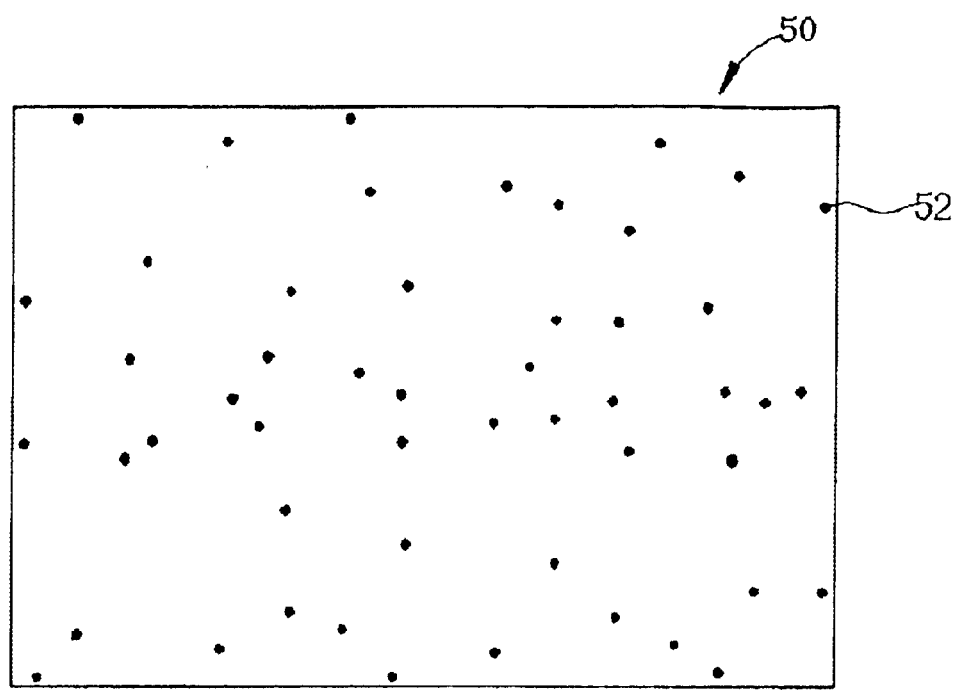
FIG. 5 is a diagram of an inspection map of a substrate.

Then, step 32 is performed to utilize a surface scan apparatus to inspect the distribution of defects on the surface of the substrate A for obtaining an inspection map. Moreover, the inspection map records at least the positions and the number of defects on the surface of the substrate A, and the inspection map can record the positions of defects in numeral type or in graphic type. Please refer to FIG. 5. FIG. 5 is a diagram showing an inspection map of a substrate. As shown in FIG. 5, there are fifty-one dots 52 on the inspection map 50, wherein each dot 52 corresponds to a defect and its location represents a specific position of the defect on the substrate A. Additionally, the surface scan apparatus records a coordinate of each dot 52, and the surface scan apparatus can output the coordinate of each dot 52 into other computer systems.

A database A is provided to store a plurality of data (step 34). Each of the data comprises a pre-determined layout of active areas and its corresponding allowable defect count. In the embodiment of the present invention, each data stored in the database A respectively corresponds to a plurality of LCDs, all of which have different dimensions. For example, each data corresponds to the layouts and the corresponding allowable defect counts of a 14.1" LCD, a 24" LCD, and a 32" LCD.

Table 1 illustrates an example of the data stored in the database A of the present invention. As shown in table 1, the database A comprises three data, and each of the three data includes a layout of active areas and its corresponding allowable defect counts. Among the three data, the first datum defines an active area according to a glass substrate required by a 16" LCD, and the allowable number of defects within the whole active areas A is 30. The second datum defines an active area B according to a glass substrate required by a 15" LCD, and the allowable number of defects within the whole active areas B is 30. The third datum defines an active area C according to a glass substrate required by a 18" LCD, and the allowable number of defects existing within the whole active areas C is 30.

Subsequently, a comparing process is performed to compare the inspection map 50 with each datum shown in table 1 for finding the data coinciding with the inspection map 50. In the embodiment of the present invention, the database A is stored in a computer system, and the above-mentioned surface scan can output the inspection map 50 into the computer system for performing the comparing process in the computer system. In addition, in another embodiment of the present invention, the database A can be stored in the above-mentioned surface scan apparatus, so that the comparing process is performed in the surface scan apparatus.

TABLE 1

| Type | Layout | Allowable defect count | Dimensions of an LCD |
|---|---|---|---|
| 1 | 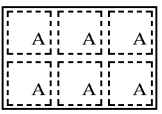 | 30 | 16" |
| 2 | 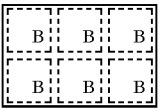 | 30 | 15" |
| 3 | 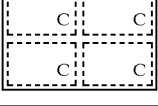 | 30 | 18" |

Figure 6A:
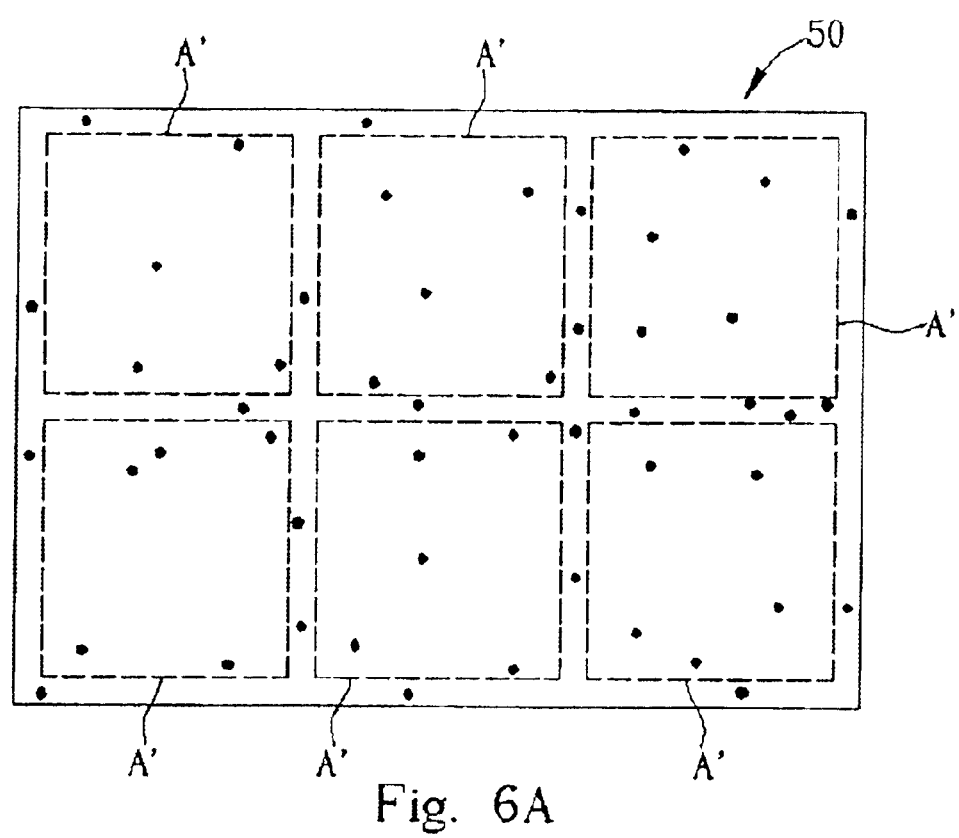
FIG. 6A is a schematic diagram showing active areas of the inspection map according to the first datum of table 1.

In the comparing process, step 36 is firstly performed to divide the inspection map into six active areas according to the first datum of table 1. As shown in FIG. 6A, FIG. 6A is a schematic diagram showing active areas of the inspection map 50 divided according to the first datum of table 1.

Step 38 is performed to count the number of defects within the six active areas A" shown in FIG. 6A, and compare the number of defects with the allowable defect count to examine whether the number of defects is smaller than or equal to 30. As a result, it can be determined whether the substrate A can be used for manufacturing a 16" LCD. The number of defects within the whole active areas A" shown in FIG. 6A is equal to 29, which is smaller than 30. Thus, step 42 is performed to record active areas of the substrate A according to the layout of the first datum.

Figure 6B:
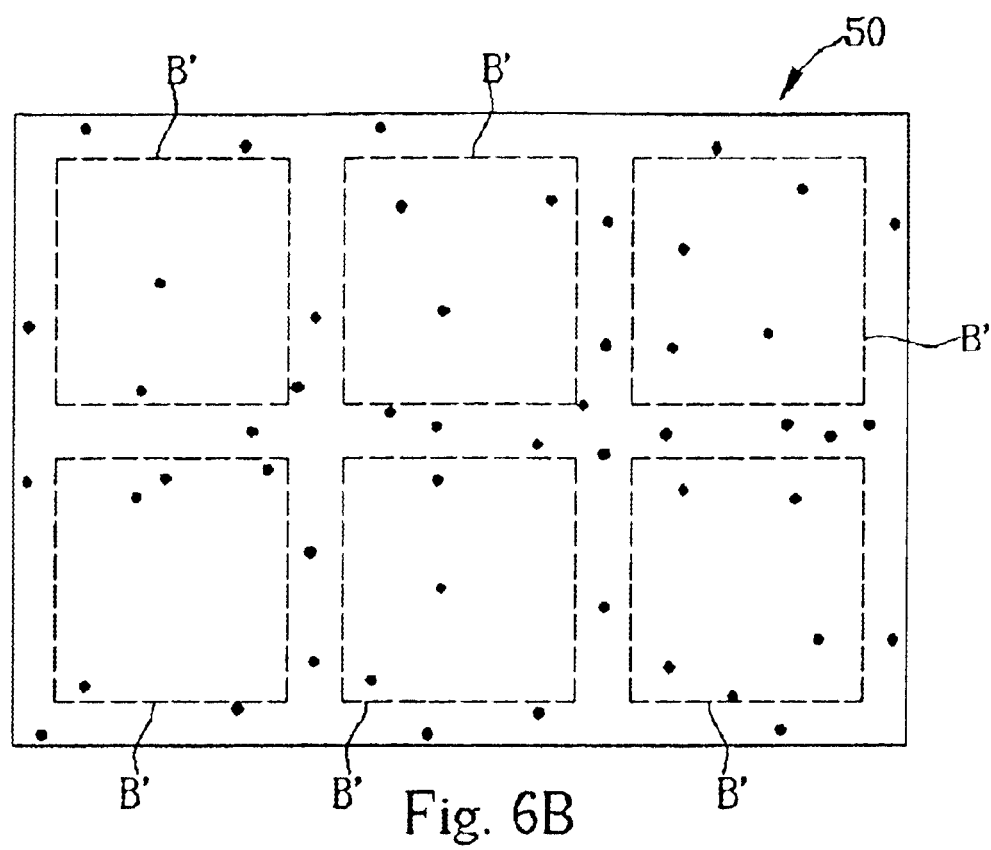
FIG. 6B is a schematic diagram showing active areas of the inspection map according to the second datum of table 1.

Thereafter, step 44 is performed to examine whether the inspection map 50 has been compared with each of the three data of table 1. If the inspection map 50 has been compared with each of the three data of table 1, step 46 is performed. However, if the inspection map 50 has not been compared with each of the three data of table 1, step 36 is repeated (noticeably, after comparing the inspection map 50 with the $N^{th}$ datum, then the inspection map 50 is compared with the $(N+1)^{th}$ datum). Up to now, the inspection map 50 is only compared with the first datum, and therefore, step 36 is repeated to divide the inspection map 50 into six active areas according to the layout of the second datum of table 1. As shown in FIG. 6B, FIG. 6B is a schematic diagram of active areas of the inspection map 50 divided according to the second datum of table 1.

Step 38 is performed to examine whether the number of defects within the six active areas B" shown in FIG. 6B coincides with the allowable defect count of the second datum (i.e. to examine whether the number of defects is smaller than or equal to 30). As a result, it can be determined whether the substrate A can be used for manufacturing a 15" LCD. The number of defects within the six active areas B" shown in FIG. 6B is equal to 21, which is smaller than 30. Thus, step 42 is performed to record active areas of the substrate A according to the layout of the second datum.

Figure 6C:
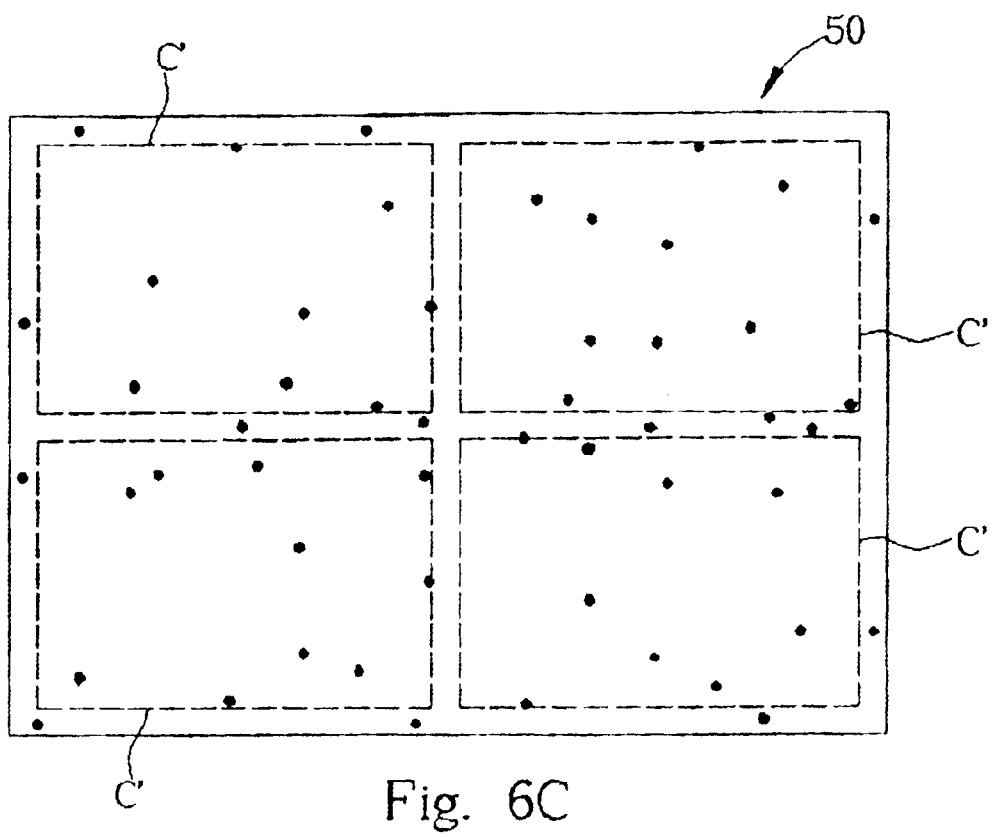
FIG. 6C is a schematic diagram showing active areas of the inspection map divided according to the third datum of table 1.

Subsequently, step 44 is performed. Because the inspection map 50 has not been compared with the third datum, step 36 is repeated to divide the inspection map 50 into four active areas according to the layout of the third datum of table 1. As shown in FIG. 6C, FIG. 6C is a schematic diagram showing active areas of the inspection map 50 divided according to the third datum of table 1.

Thereafter, step 38 is performed to examine whether the number of defects within the four active areas C" shown in FIG. 6C coincides with the allowable defect count of the third datum (i.e. to examine whether the number of defects is smaller than or equal to 30). The number of the defects within the four active areas C" shown in FIG. 6C is 37, which is larger than 30, so that step 40 is performed to examine whether the inspection map 50 has been compared with each of the three data of table 1.

Since the inspection map 50 has been compared with the three data of table 1, step 46 is performed to classify the substrate A. Firstly, the substrate A is classified into a classification selecting from the group of a 16" type, a 15" type, an 18" type and a scrapped type. Then, active areas of the substrate A are defined according to the classification of the substrate A. Finally, the substrate 30 is stored in a pre-determined place (e.g. in a warehouse or beside a production machine). As described above, when the inspection map 50 coincides with the first datum and the second datum of the database A concurrently, the first datum and the second datum have to be sorted according to priority for determining a preferable datum. Then, the active areas of the substrate A are defined according to the layout of the preferable datum.

The priority of sorting can be determined according to (1) the number of defects of the whole active areas; and (2) the market requirements of LCDs, for example. Based on the first method, in the above-mentioned comparing process, the inspection map 50 coincides with the first datum and the second datum. That is, the substrate A can be used for manufacturing a 16" LCD or a 15" LCD. The number of defects (21/piece) of the whole active areas B" shown in FIG. 6B is smaller than the number of defects (29/piece) of the whole active areas A" shown in FIG. 6A, so that the second datum is regarded as a preferable datum. Then, the active areas of the substrate A are defined according to the layout of the second datum. Additionally, according to the second method, if a market requirement for a 16" LCD is bigger than a market requirement for a 15" LCD, the first datum is therefore regarded as a preferable datum. Then, the active areas of the substrate A are defined according to the layout of the first datum.

Furthermore, as shown in FIG. 4, when a substrate does not coincide with any of the data stored in the database A, the substrate would be classified as a scrapped type in step 46 of the classifying process.

The database A of table 1 is utilized for explaining the practice of the present invention. However, the database A is not limited to that shown in table 1. Actually, the amount of data stored in the database A can be expanded according to practical requirements. Moreover, the allowable number of defects, i.e. allowable defect count, of each data is not limited to 30, and it can be adjusted according to process requirements. For example, dimensions of an LCD include 14.1", 15", 16", 17", 18", 19", 20", 22", 24", 28", 30", and 32". As a result, the database A can include all kinds of layouts and allowable defect counts corresponding to the LCDs of the above-mentioned dimensions.

In brief, the present invention firstly utilizes a surface scan apparatus to scan a glass substrate for obtaining an inspection map of the glass substrate. Then, the inspection map is divided into some active areas according to the layouts of each of the data stored in the database. Thereafter, the defect counts within the active areas of the inspection map are compared with the corresponding allowable defect count. Then, active areas of the glass substrate are defined according to the layouts of the data coincided with the inspection map. Finally, the substrate is classified and stored.

The present invention is to compare the defect counts within active areas of a glass substrate with the corresponding allowable defect count of the glass substrate. Since locations of active areas of a glass substrate are defined according to a size of an LCD, active areas corresponding to each type of LCD are positioned at different regions on the glass substrate. Accordingly, even though the glass substrate is not suitable for manufacturing an 18" LCD, it still may be suitable for fabricating a 15" LCD. As a result, each glass substrate can be utilized more effectively, and the yield of the glass substrate is further enhanced.

Those skilled in the art will readily observe that numerous modifications and alterations of the device may be made while retaining the teachings of the invention. Accordingly, the above disclosure should be construed as limited only by the metes and bound of the appended claims.

What is claimed is:

1. A method for classifying a substrate comprising:

providing a substrate;

producing an inspection map of the substrate;

providing a database having a plurality of data, each of the data having a layout of active areas and its corresponding allowable defect count; and dividing the inspection map according to each of the layouts of active areas, wherein the divided inspection map is compared with the corresponding allowable defect count of each of the layouts of active areas for classifying the substrate.

2. The method of claim 1 wherein the database is stored in a computer system.

3. The method of claim 1 wherein a method for producing the inspection map comprises:

scanning a plurality of sub-regions of the substrate by using a surface scan apparatus for inspecting defects within the sub-regions and their corresponding positions; and recording the defects of the surface of the substrate and their corresponding positions for producing the inspection map.

4. The method of claim 3 wherein the database is stored in the surface scan apparatus.

5. The method of claim 1 wherein the substrate is a glass substrate of a flat panel display, and the data of the database corresponds to layouts of active areas and their corresponding allowable defect counts of glass substrates of a plurality of types of flat panel displays.

6. The method of claim 5 wherein the surface of the glass substrate is covered with at least a thin film, and the thin film is chromium (Cr) or indium tin oxide (ITO).

7. A method for defining active areas of a substrate and classifying the substrate comprising:

provading a substrate and its corresponding inspection map;

providing a database having a plurality of data, each of the data having a pre-determined layout of active areas and its corresponding allowable defect count; and performing a comparing process to compare the inspection map with each of the data for selecting at least one datum coinciding with the inspection map, defining the active areas of the substrate according to the layout of active areas of the datum coinciding with the inspection map, and classifying a classification of the substrate.

8. The method of claim 7 wherein the comparing process comprises comparing the inspection map with the corresponding allowable defect count of each of the data for selecting the datum whose allowable defect count is larger than the inspection map.

9. The method of claim 8 wherein the datum coinciding with the inspection map is a datum whose allowable defect count is larger than the inspection map.

10. The method of claim 9 wherein when more than one datum coincide with the inspection map, the data coinciding with the inspection map are sorted according to priority for determining a preferable datum, the active areas of the substrate are defined according to the layout of the preferable datum, and the substrate is classified and stored.

11. The method of claim 9 wherein the database is stored in a computer system and the comparing process is performed in the computer system.

12. The method of claim 9 wherein a method for producing the inspection map comprises:

scanning a plurality of sub-regions of the substrate by using a surface scan apparatus for inspecting defects within the sub-regions and their corresponding positions; and recording the defects of the surface of the substrate and their corresponding positions for producing the inspection map.

13. The method of claim 12 wherein the database is stored in the surface scan apparatus, and the comparing process is performed by the surface scan apparatus.

14. The method of claim 9 wherein the substrate is a glass substrate of a flat panel display, and the plurality of data of the database corresponds to layouts and their corresponding allowable defect counts of glass substrates of a plurality of types of flat panel displays.

15. The method of claim 14 wherein the surface of the glass substrate is covered with at least a thin film, and the thin film is chromium (Cr) or indium tin oxide (ITO).

16. A method for defining active areas of a substrate comprising:

providing a substrate;

scanning the substrate for obtaining an inspection map;

providing a database having a plurality of data, each of the data having a pre-determined layout of active areas and its corresponding allowable defect count;

dividing the inspection map according to the layout of active areas; and comparing the inspection map with the corresponding allowable defect count when the inspection map is smaller than or equal to the corresponding allowable defect count of the layout of active areas, and defining the active areas of the substrate according to the layout of active areas.

17. The method of claim 16 wherein the database is stored in a computer system.

18. The method of claim 16 wherein a method for scanning the substrate comprises:

scanning a plurality of sub-regions of the substrate by using a surface scan apparatus for inspecting defects within the sub-regions and their corresponding positions; and recording the defects of the surface of the substrate and their corresponding positions for producing the inspection map.

19. The method of claim 18 wherein the database is stored in the surface scan apparatus.

20. The method of claim 16 wherein the substrate is a glass substrate of a flat panel display, and the plurality of data of the database corresponds to layouts and their corresponding allowable defect counts of glass substrates of a plurality of types of flat panel displays.

21. The method of claim 20 wherein the surface of the glass substrate is covered with at least a thin film, and the thin film is chromium (Cr) or indium tin oxide (ITO).

* * * * *